(12) United States Patent
Hjort et al.

(10) Patent No.: US 9,283,433 B2
(45) Date of Patent: Mar. 15, 2016

(54) STAND-ALONE THERAPEUTICAL TRAINING DEVICE

(75) Inventors: Martin Hjort, Hornslet (DK); Tanja Aabo Pedersen, Vejle (DK)

(73) Assignee: INNOVAID A/S, Egç (DK)

( * ) Notice: Subject to any disclaimer, the term of this patent is extended or adjusted under 35 U.S.C. 154(b) by 82 days.

(21) Appl. No.: 14/128,165

(22) PCT Filed: Jun. 29, 2012

(86) PCT No.: PCT/DK2012/000077
§ 371 (c)(1),
(2), (4) Date: Feb. 20, 2014

(87) PCT Pub. No.: WO2013/000466
PCT Pub. Date: Jan. 3, 2013

(65) Prior Publication Data
US 2014/0152450 A1    Jun. 5, 2014

(30) Foreign Application Priority Data

Jun. 30, 2011 (DK) .................................. 201100491

(51) Int. Cl.
*A63B 24/00* (2006.01)
*A63B 23/04* (2006.01)
(Continued)

(52) U.S. Cl.
CPC ............ *A63B 24/0062* (2013.01); *A61B 5/1036* (2013.01); *A61B 5/1116* (2013.01); *A63B 23/0355* (2013.01); *A63B 23/0458* (2013.01); *A63B 26/003* (2013.01);
(Continued)

(58) Field of Classification Search
CPC .... A63B 71/00; A63B 24/00; A63B 24/0062; A63B 23/0458; A63B 23/0355; A63B 69/0053; A63B 26/003; A63B 71/0622; A63B 2071/0027; A63B 2071/0625; A63B 2071/0652; A63B 2071/0655; A63B 2209/08; A63B 2220/51; A63B 2225/20; A63B 2225/50; A63B 2230/01; A61B 5/1116; A61B 5/1036
USPC ......... 340/573.1, 665, 539.1, 539.11, 539.12, 340/666, 815.45, 407.1, 384.1; 482/8, 79
See application file for complete search history.

(56) References Cited

U.S. PATENT DOCUMENTS 2,490,150 A * 12/1949 Newton, Jr. ..................... 60/368
4,534,557 A * 8/1985 Bigelow et al. ............... 473/442
(Continued)

FOREIGN PATENT DOCUMENTS

EP         0210501 A2    2/1987
EP         2105091 A1    9/2009

*Primary Examiner* — Daniel Wu
(74) *Attorney, Agent, or Firm* — Dinsmore & Shohl LLP; Weston R. Gould

(57) ABSTRACT

The present invention relates to a stand-alone therapeutical training device which is peculiar in that the stand-alone therapeutical training device comprising a shallow housing having at least a top surface and a bottom surface, said housing comprising at least one force sensor, said force sensor measuring the force applied to said top surface of said housing and generating a response signal, at least one user feedback unit, a controller placed inside said housing configured for controlling said user feedback unit and that the controller controls the user feedback unit proportionally to said response signal from said force sensor. Hereby can be archived a simple stand-alone therapeutically training device enabling the patient and/or the physiotherapist to evaluate the force or weight applied by the user on the upper surface of the device.

15 Claims, 15 Drawing Sheets

(51) Int. Cl.
*A63B 69/00* (2006.01)
*A63B 26/00* (2006.01)
*A63B 71/06* (2006.01)
*A61B 5/11* (2006.01)
*A63B 23/035* (2006.01)
*A61B 5/103* (2006.01)
*A63B 71/00* (2006.01)

(52) U.S. Cl.
CPC ........ *A63B 69/0053* (2013.01); *A63B 71/0622* (2013.01); *A63B 2071/0027* (2013.01); *A63B 2071/0625* (2013.01); *A63B 2071/0652* (2013.01); *A63B 2071/0655* (2013.01); *A63B 2209/08* (2013.01); *A63B 2220/51* (2013.01); *A63B 2225/20* (2013.01); *A63B 2225/50* (2013.01); *A63B 2230/01* (2013.01)

(56) References Cited

U.S. PATENT DOCUMENTS

| | | | | |
|---|---|---|---|---|
| 4,928,959 | A  * | 5/1990  | Bassett et al. | 482/79 |
| 6,110,073 | A    | 8/2000  | Saur et al. | |
| 6,122,846 | A    | 9/2000  | Gray et al. | |
| 8,241,183 | B2 * | 8/2012  | Hautoplund | 482/8 |
| 2003/0073541 | A1   | 4/2003  | Carlson | |
| 2006/0117860 | A1 * | 6/2006  | Kurtz | 73/754 |
| 2007/0021282 | A1   | 1/2007  | Karp | |
| 2008/0161796 | A1 * | 7/2008  | Cao et al. | 606/41 |
| 2010/0321310 | A1 * | 12/2010 | Kim et al. | 345/173 |
| 2014/0132572 | A1 * | 5/2014  | Rusanen et al. | 345/178 |

* cited by examiner

STAND-ALONE THERAPEUTICAL TRAINING DEVICE

CROSS-REFERENCE TO RELATED APPLICATIONS

This application is the U.S. National Phase of PCT/DK2012/000077 filed Jun. 29, 2012, which claims priority of Danish Patent Application PA201100491 filed Jun. 30, 2011.

FIELD OF THE INVENTION

The present invention relates to a stand-alone therapeutical training device or exercise equipment allowing the user to perform interactive training or exercises with an audio, visual and/or tactile feedback to the user and/or therapist. The present invention is mainly to be used as a part of training or exercise sessions in a rehabilitation facility or at home.

BACKGROUND OF THE INVENTION

Individuals recovering from a surgery or e.g. a brain injury (stroke) need physical and optionally cognitive therapy and training. Today, training is mainly carried out by simple exercises where a patient interacts with a physiotherapist and uses non-feedback training devices and tools like stepping on mats in different colours and other like activity tools. These non-feedback devices lack an important feature of giving feedback to both the physiotherapist and the user on his/her performance. Such feedback may include an audiovisual signal indicating how an exercise is carried out e.g. by the means of a light source and/or a loudspeaker. The physiotherapist has difficulties evaluating e.g. the weight distribution on the patient's legs, whether the patient has all his/her body weight on one leg or it is evenly distributed on both legs.

One the other hand very complex interactive systems exist on the market today, such as interactive horizontal video screens, where a person can interact with the system by walking around on the horizontal screen and hereby receive a response on the screen according to his/her movements.

EP 2 105 09 01 A1 relates to a therapeutic training device comprising a shallow housing of a specific shape with a quadratic top surface, a quadratic bottom surface and four thin rectangular side surfaces. The housing comprising an upwardly open cavity in the top surface and a flexible and transparent cover has a size in the range between the size of a human first and a human foot, and defines a central part. The force sensor measures the force applied on the flexible and transparent cover and generates a response signal. The housing further comprises a light source placed inside the cavity, the light source being visible though the flexible and transparent cover and a central processor placed inside the housing, which activates the light sources in accordance with a specific software and evaluates the response signal from the force sensor in accordance with the specific software. A plurality of communication means is located on the side surfaces and is controlled by the central processor and communicates with adjacent devices.

U.S. Pat. No. 4,928,959 relates to a method and device for providing active exercise treatment for a patient suffering from a bone disorder, where a patient strikes a sensor in a manner to produce an impact load at an impact rate along the axis of a bone experiencing the bone disorder, and that impact load and impact rate are measured and compared to desired impact load and impact rate values to determine a success indicator of how close the patient came to the desired impact load and impact rate values in striking the sensor. The success indicator is provided to the patient as feedback for the active exercise treatment and is recorded.

U.S. Pat. No. 6,122,846 relates to an apparatus and method of operation for measuring forces applied to a wearer's foot, the apparatus providing an indication to the wearer when forces on the foot exceed pre-selected upper limits or do not meet pre-selected lower limits. A body member is disclosed for attachment around the wearer's foot, the body member having an exterior sole and an interior sole portion covered by a rigid foot plate. The foot plate includes an upper support surface for contact with the foot. The interior sole portion includes at least one cavity within, with a force sensing unit attachable partially within the cavity. At least one strain gage is positioned at a midpoint on the force sensing unit, and the force sensing unit is connectable to the underside of the foot plate. An electronic means is mounted within the cavity and is electrically connected to the at least one strain gage. The electronic means receives electronic signals from the strain gage, the signals in proportion to force applied onto the force sensing unit when the wearer's foot applies weight onto the foot plate, with conversion of the signals to output signals for transmission to a signal processing means in a remotely located receiver and display unit. The display unit compares the output signals to upper limits and lower limits, and displays alarms when output signals do not reach lower limits, or exceed upper limits, therefore assisting with therapeutic rehabilitation of an injured lower extremity.

US2007/021282 relates to a postural awareness apparatus includes a pad, a signal generating element and an element for detecting a weight applied to the pad and activating the signal generating element when the weight so detected exceeds a predetermined weight.

SUMMARY OF THE INVENTION

The present invention shall help and facilitate physiotherapists and individuals doing exercises and training by providing feedback signals based upon the user interactions in a simple manner. The object of the invention is to offer a simple stand-alone therapeutically training device enabling the patient and/or the physiotherapist to evaluate the force or weight applied by the user on the top surface of the device.

A further object of the invention is to offer a tool for evaluating the force or weight distribution between left and right foot and/or left and right hand. By using two stand-alone therapeutical devices the user stands on them having one foot on each device, the physiotherapist and/or the user is able to evaluate this force or weight distribution by monitoring the user feedback signal from each of the therapeutical training devices, which is proportional to the force or weight applied to top surface of each of them.

A further object of the invention is to offer a tool for evaluation the force or weight distribution between the heel and toe and/or the palm and fingertips. By using one or more standalone therapeutical devices the user stands on at least one of them with at least one foot on a device, the physiotherapist and/or the user is able to evaluate this force and/or weight distribution between the heel and toes by monitoring the user feedback signal from the therapeutical training devices, which is proportional to the force or weight distribution between the heel and toe end of the top surface of a device.

A further object of the invention is to offer a simple therapeutically training system based on the use of multiple stand-alone therapeutical training devices, these devices being independently operated and controlled. A number of different coloured overlays are attached to the devices so the devices appear as differently coloured platforms. A pseudo random feedback signal is generated, preferably a light signal, upon activating of the force sensor of each of the devices by stepping on a device. This device indicates a pseudo random colour directing the user to step to the next device matching the colour of the feedback signal generated. By having more stand-alone therapeutical training devices lying on the floor with the top surface facing the user, configured as step stones defining a path to walk, the user may be directed by this pseudo random signal to the next step stone or device.

Furthermore the present invention has the purpose of motivating the person using it by interactive training and exercises by a simple visual, audio and/or tactile feedback. The stand-alone therapeutical training device can be used by any person, but is mostly intended to be used by persons suffering from cerebrovascular (stroke) accident, different handicaps or diseases e.g. spastic hemiplegia, diplegia or tetraplegia, Parkinson's disease and Creutzfeldt-Jakob disease.

In a first aspect the present invention relates to a stand-alone therapeutical training device where the object can be achieved by the stand-alone therapeutical training device as specified in the preamble of claim 1 which is peculiar in that the stand-alone therapeutical training device comprising a shallow housing having at least a top surface and a bottom surface, said housing comprising at least one force sensor, said force sensor measuring the force applied to said top surface of said housing and generating a response signal, at least one user feedback unit, a controller placed inside said housing configured for controlling said user feedback unit characterised in that the controller is adapted to control the user feedback unit proportionally to said response signal from said force sensor and that the controller is adapted to control the user feedback unit in such way that a pseudo random feedback signal is generated, upon activating of the force sensor of the device.

Hereby can be achieved a stand-alone therapeutical training device enabling users and/or physiotherapists evaluating the force and/or the weight applied to the device by the user. Proportional meaning within a specified working range of the measured force a giving measured force or weight equals a giving signal level of the response signal hence a giving signal level of the user feedback signal whereas another giving signal level of the response signal hence a giving another signal level of the user feedback signal.

A specified working range is preferably a weight within a range from zero to the weight of a human person. Preferably this range is adjustable by the user via the user interface.

By having one or more stand-alone therapeutical training devices lying on the floor with the top surface facing the user, the user may stand onto one or two therapeutical training device one foot on each, hereby can be achieved an indication of how the user's weight is distributed on each leg.

By having one or more stand-alone therapeutical training devices hanging on a wall with the top surface facing the user, the user may press his/her hands against one or two therapeutical training device one hand on each, hereby can be achieved an indication of how the user's weight or force is distributed on each hand.

Stand-alone meaning the therapeutical training device is independently operated and controlled and the therapeutical training device does not need to be a part of a larger integrated system. However multiple stand-alone therapeutical training devices may be used simultaneously as individual units or devices.

The user feedback unit may be any means of signalling a signal to the user including but not limited to a visual, audio and/or tactile signal to be interpreted by the user.

The user may be the actual person interacting with the therapeutical training device and/or a supervisory person e.g. a physiotherapist.

Hereby can be archived a simple stand-alone therapeutically training device enabling the patient and/or the physiotherapist to evaluate the force or weight applied by the user on the top surface of the device.

By having the controller adapted to control the user feedback unit in such way that a pseudo random feedback signal is generated, upon activating of the force sensor of the device it hereby can be archived a mean of motivating the user to move his/her hands or feet to a new position touching or standing on another therapeutical training device. By having more stand-alone therapeutical training devices lying on the floor with the top surface facing the user, configured as step stones defining a path to walk, the user may be directed by this random signal to the next step stone or device. Preferrably the random signal is a light signal of a predefined set of different colours matching the different colours of different stand-alone therapeutical training devices.

By having more stand-alone therapeutical training devices hanging on a vertical surface with the top surface facing the user, configured as touch pads, the user touches one device and may be directed by this random signal to the next touch pad or device. Preferably the random signal is a light signal of a predefined set of different colours matching the different colours of different stand-alone therapeutical training devices.

Optionally one or more users may use the devices simultaneously during a training or exercise session.

Optionally the therapeutical training device further comprises at least one magnet for enabling the device to be easily attached to a vertical metal surface.

Optionally the therapeutical training device further comprises a means for wireless communication. The wireless communication means is configured to transmit the signal obtained at one or more of the force sensors to another device and/or central interface unit.

Optionally the wireless communication means is configured to receive a signal from another device or central interface unit to control the user feedback unit of the device. Such central interface unit could be a tablet, computer or gaming device. The means for wireless communication could be any infra- and/or ultra sound, infra red diodes and/or radiofrequency (RF) transmitters and/or receivers.

The present invention differs from prior art by having at least two different operation modes; one operation mode where the controller controls the user feedback unit proportionally to the force or weight applied at the top of the surface of the device and another operation mode where a pseudo random signal is generated upon activation of the force sensor of the device. By combining two or more operation modes into the device, the stand-alone therapeutical device will become a multifunctional device hence saving cost and obtain added value to the users. Furthermore synergies such as cost savings and time savings can be obtained by using the same device for both weight transfer and balance exercises by the proportional response signal and visio motor control exercises by the pseudo random function. Hereby the therapists do not need to have two or more different types of therapeutical training devices and can easily change the objective of the exercise by changing the operation mode of one or more stand-alone therapeutical training devices on the user interface of the device.

Optionally the user feedback unit comprises at least one light source hereby can be achieved a light signal where the intensity of the light is proportional to the force or weight applied to the top surface of the therapeutical training device.

Optionally the user feedback unit comprises more than one light source configured as a visual scale indicating the force or weight applied to the top surface of the therapeutical training device by switching on and/or off a number of light sources proportional to the force applied.

Optionally the light source is a light emitting diode hereby can be achieved a power efficient visual feedback indicator.

Optionally the light source comprises multiple light emitting diodes in different colours hereby can be achieved a coloured visual scale indicating the force or weight applied to the top surface of the therapeutical training device by switching on and/or off a number of light sources in different colours proportional to the force applied.

Optionally the light source comprises at least one multicoloured light emitting diode hereby can be achieved a multicoloured visual scale indicating the force or weight applied to the top surface of the therapeutical training device by altering the colour of the scale e.g. from red to blue in accordance with the light spectrum proportional to the force applied. Hereby is obtained a visual indication of the weight and/or force applied which is easy to interpret. Optionally other light scales and/or colours may be applied.

Optionally the user feedback unit comprises at least one loudspeaker hereby can be achieved an audio feedback to the user indicating the force or weight applied to the top surface of the therapeutical training device by altering the tone or frequency proportional to the force applied. This may be useful if the user is blind or has low vision. Optionally the user feedback unit comprises at least one loudspeaker hereby can be achieved an audio feedback to the user indicating the force or weight applied to the top surface of the therapeutical training device by altering the amplitude an audio signal proportional to the force applied. This can be used as an alternatively audio signalling.

Optionally the loudspeaker is a piezoelectric loudspeaker.

Optionally the user feedback unit comprises at least a vibrator hereby can be achieved a tactile feedback to the user indicating the force or weight applied to the top surface of the therapeutical training device by altering the frequency or vibration pattern proportional to the force applied. This may help users to receive the feedback signal in a tactile manner, which could be useful to stimulate the user physically.

Optionally the user feedback unit comprises at least a vibrator hereby can be achieved a tactile feedback to the user indicating the force or weight applied to the top surface of the therapeutical training device by altering the amplitude of the vibration proportional to the force applied.

Optionally the force sensor is a force sensitive pad placed on top of said top surface of said housing hereby can be achieved a flat implementation of a force sensor with minimal height. The force sensitive pad being any material able to change at least one electric parameter as a function of the force applied to the surface of it. An electric parameter may be a resistance, inductance or capacitance.

Optionally the force sensor is a strain gauge placed inside said housing hereby can be achieved an alternative implementation of a force sensor. The strain gauge being any component able to change at least one electric parameter as a function of the force applied to the surface of it. An electric parameter may be a resistance, inductance or capacitance.

Optionally a force distribution acryl sheet is placed on top of the force sensor to adjust the sensitivity of the force sensor.

Optionally the stand-alone therapeutical training device comprises at least two force sensors or a force sensor pad with at least two force sensing areas.

The two forces sensors or sensor pad is configured to measure the force and/or weight applied to the top surface of the device in such way that the signals from the sensors are proportional to the weight or force applied at the heel and the toes and/or the palm and fingertips. Hereby can be achived two signals indicating the weight and/or force applied to the device at the heel and at the toes and/or at the palm and/or fingertips.

Optionally the controller of the stand-alone therapeutical training device is further adapted to control the user feedback unit proportionally to the difference in weight or force applied at at least two force sensors or two force sensing areas.

Hereby can be achieved a signal to indicate how the weight or force is distributed between the heel and toes and/or the palm and fingertips. This may be useful when training the balance and postural control of the body. Furthermore this by adding this control mode to the device, it will become even more useful without adding extra cost. Optionally the therapeutical training device further comprises a transparent cover to protect the user feedback unit.

Optionally the therapeutical training device further comprises a user interface for adjusting the specified working range by pressing plus and minus buttons.

Optionally the therapeutical training device further comprises a user interface for selecting different operation modes such a specific working range to be used when using the device for hand activation, another working range to be used for foot activation and random mode.

Optionally the therapeutical training device further comprises a second force sensor on the bottom of the bottom surface configured for measuring the force acting on the bottom side of the therapeutical training device and generating a second response signal. Optionally the controller controls the user feedback unit based on the second response signal from force sensor on the bottom surface. Hereby an alternative sensor input may be used for some or all of the same functionally as applies to the first force sensor on the top surface, giving the therapeutical training device different functions each side.

Optionally the therapeutical training device further comprises at least one magnet for enabling the device to be easily attached to a vertical metal surface. Optionally the therapeutical training device further comprises a means for wireless communication. The wireless communication means is configured to transmit the signal obtained at one or more of the force sensors to another device and/or central interface unit. Optionally the wireless communication means is configured to receive a signal from another device or central interface unit to control the user feedback unit of the device. Such central interface unit could be another user interface, a tablet computer, computer or gaming device. The means for wireless communication could be any infra- and/or ultra sound, infrared diodes and/or radiofrequency (RF) transmitters and/or receivers.

In another aspect the present invention relates to a method of providing means of feedback to the user and/or physiotherapist during training which is peculiar in that that at least the following steps are performed:

a: perform a measurement of the force applied by the user on the top surface of a stand-alone therapeutical training device.

b: control at least one user feedback unit based on said measured force applied c: the user feedback unit indicates a signal to the user which is proportional to the force applied to the top surface of the stand-alone therapeutical training device.

The stand-alone therapeutical training device being a device having some or all of the functionality of the present invention.

In a third aspect the present invention relates to the use of a stand-alone therapeutic training device training or exercise equipment for individuals having the need of physical training.

In a fourth aspect the present invention relates to a stand-alone therapeutical training device where the object can be achieved by a stand-alone therapeutical training device as specified in the preamble of claim 1 which is peculiar in that the stand-alone therapeutical training device comprising a shallow housing having at least a top surface and a bottom surface, said housing comprising, at least one force sensor, said force sensor measuring the force applied to said top surface of said housing and generating a response signal, at least one user feedback unit, a controller placed inside said housing for controlling said user feedback unit and that the controller controls the user feedback unit randomly to said response signal from said force sensor.

Hereby can be archived a mean of motivating the user to move his/her hands or feet to a new position touching or standing on another therapeutical training device.

By having more stand-alone therapeutical training devices lying on the floor with the top surface facing the user, configured as step stones defining a path to walk, the user may be directed by this random signal to the next step stone or device. Preferably the random signal is a light signal of a predefined set of different colours matching the different colours of different stand-alone therapeutical training devices.

By having more stand-alone therapeutical training devices hanging on a vertical surface with the top surface facing the user, configured as touch pads, the user touches one device and may be directed by this random signal to the next touch pad or device. Preferably the random signal is a light signal of a predefined set of different colours matching the different colours of different stand-alone therapeutical training devices.

Optionally one or more users may use the devices simultaneously during a training or exercise session.

Optionally the therapeutical training device further comprises at least one magnet for enabling the device to be easily attached to a vertical metal surface.

Optionally the therapeutical training device further comprises a means for wireless communication. The wireless communication means is configured to transmit the signal obtained at one or more of the force sensors to another device and/or central interface unit. Optionally the wireless communication means is configured to receive a signal from another device or central interface unit to control the user feedback unit of the device. Such central interface unit could be a tablet, computer or gaming device. The means for wireless communication could be any infra- and/or ultra sound, infra red diodes and/or radiofrequency (RF) transmitters and/or receivers. It is to be noticed that the term comprising, used in the present description and claims should not be interpreted as being restricted to the means listed thereafter; it does not exclude other elements or steps. Thus, the scope of the expression a device comprising means A and B should not be limited to devices consisting of only components A and B. It means that with respect to the present invention, the only relevant components are A and B.

DETAILED DESCRIPTION OF EMBODIMENTS OF THE INVENTION

Figure 1:
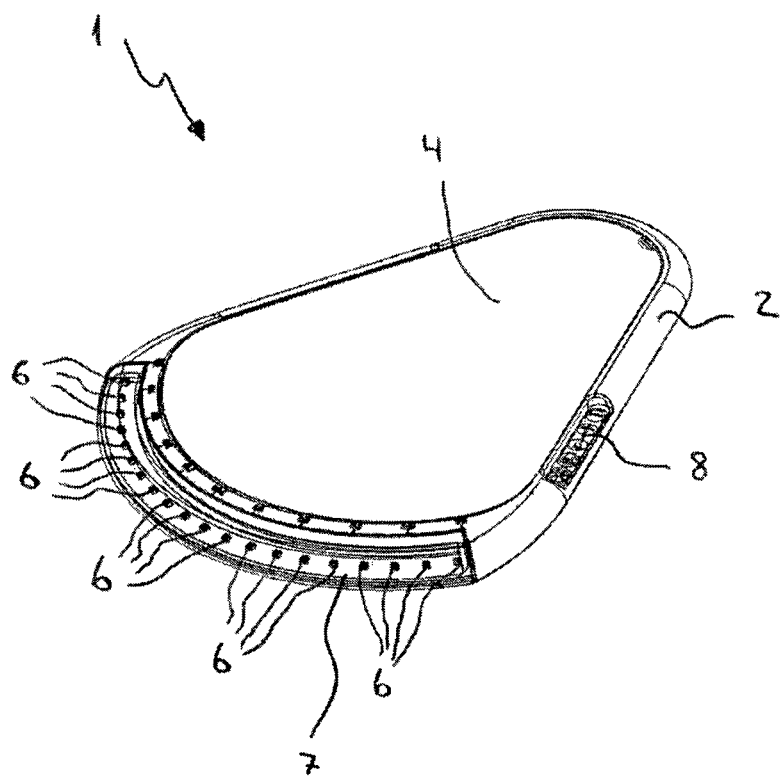
FIG. 1: The stand-alone therapeutic training device according to the present invention in a perspective view from top/left side.

Referring to FIG. 1, the stand-alone therapeutic training device (1) is shown in a top/left side view. The housing (2) encapsulates the controller, battery compartment and user feedback units (6). A transparent cover (7) protects the user feedback units (6). The user interface (8) is situated on the left side of the housing (2) and may be used for selecting different operational modes of the device and different working ranges for the force/weight scale. A force sensor pad (4) is place on the top surface (112, FIG. 2) of the device (1).

Figure 2:
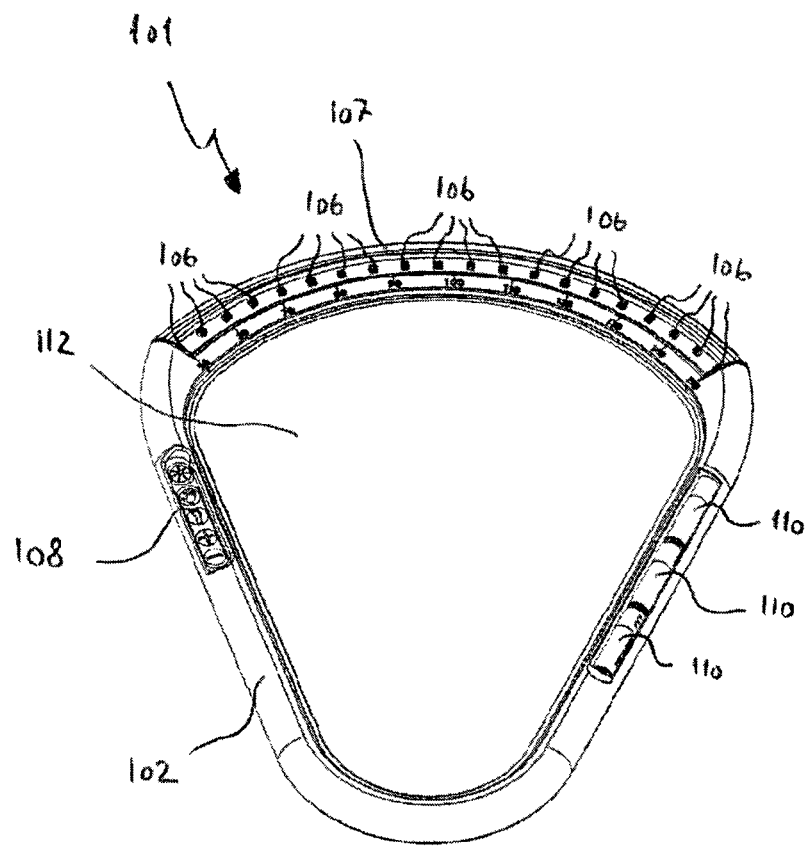
FIG. 2: A detail of the present invention in a perspective view from the top without the force sensor pad and battery compartment lid.

Referring to FIG. 2, the stand-alone therapeutic training device (101) is shown in a top view without the force sensor pad (4, FIG. 1) and battery compartment lid. The three batteries (110) powering the device (101) are shown. The housing (102), transparent cover (107) and a number of user feedback units (106) are also shown.

Figure 3:
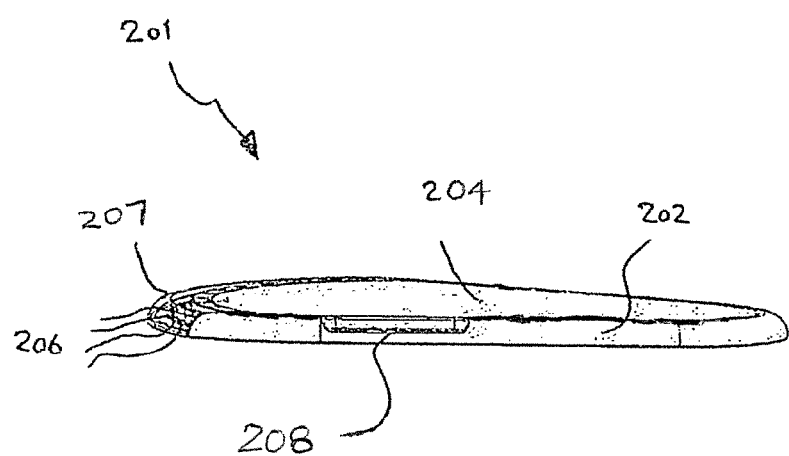
FIG. 3: A detail of the present invention in a perspective view from the left side.

Referring to FIG. 3, the stand-alone therapeutic training device (201) is shown in a left side view. The housing (202), force sensor pad (204), transparent cover (207) and a number of user feedback units (206) are also shown in FIG. 3.

Figure 4:
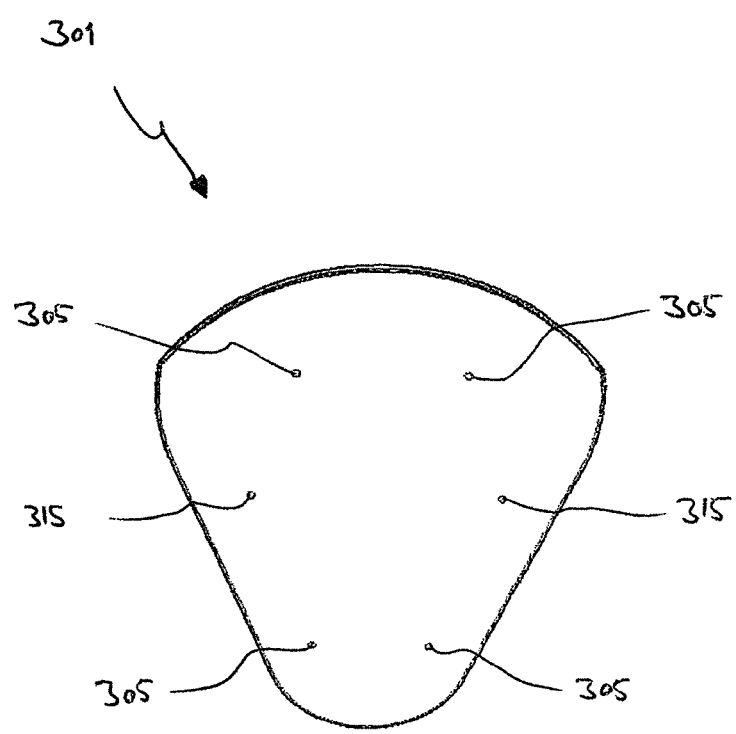
FIG. 4: A detail of the present invention in a perspective view from the bottom side.

Referring to FIG. 4, the stand-alone therapeutic training device (301) is shown in a bottom view where four assembly screws (305) and two holes (315) for wall mounting can be seen on the bottom surface (303).

Figure 5:
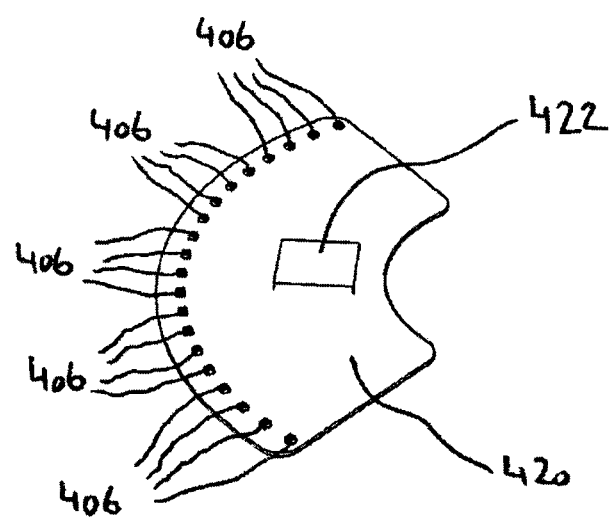
FIG. 5: A detail of the controller of the present invention.

Referring to FIG. 5, a detail of the controller (420) of the stand-alone therapeutic training device (1, FIG. 1) where a number of user feedback units (406) and an integrated circuit (422) is shown. The integrated circuit being a part of the controller (420).

Figure 6:
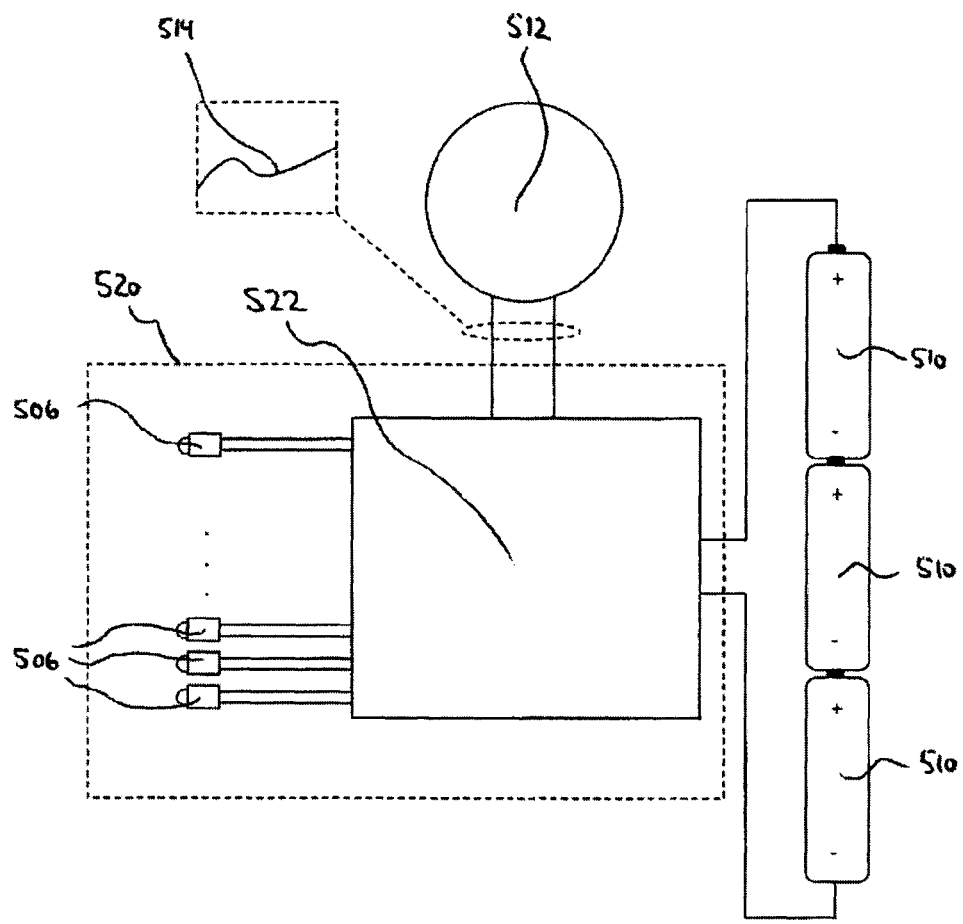
FIG. 6: A block schematic of the electrical system of the present invention.

Referring to FIG. 6, A block schematic of the electrical system of the present invention showing the controller (520), the batteries (510) powering the device, the force sensor (512), the integrated circuit (522) and a number of user feedback units (506). The force sensor (512) generates an electric response signal (514) based on the measures force or weight applied to the top surface (112, FIG. 2) of the device (1, FIG. 1), the controller (520) converts this signal and controls the user feedback units (506) accordingly. The integrated circuit (522) is a part of the controller (520).

Figure 7:
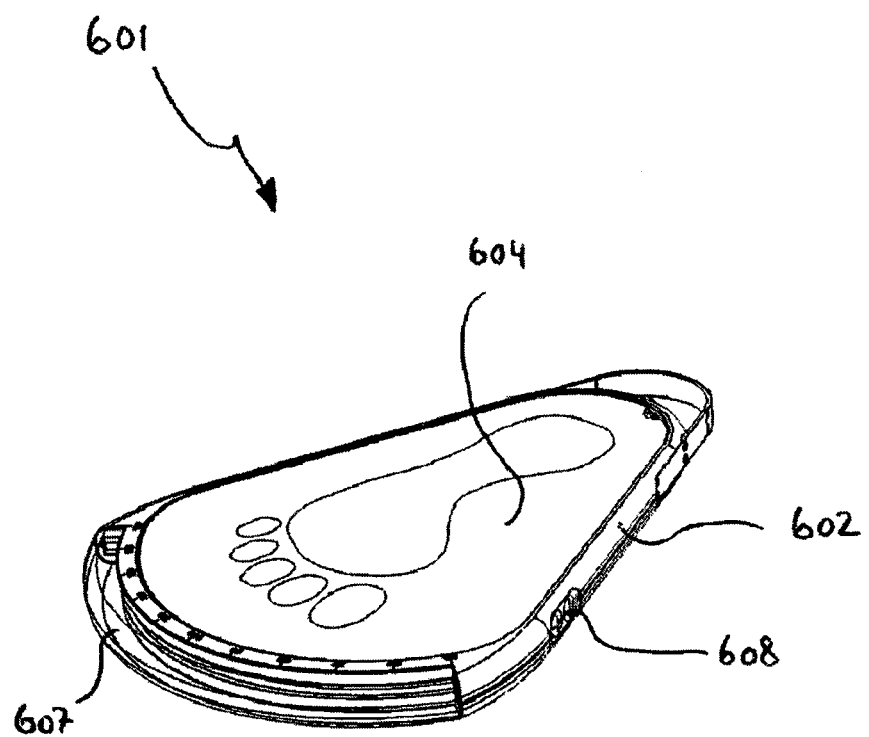
FIG. 7: A second embodiment of the present invention in a perspective view from top/left side.

Referring to FIG. 7, A second embodiment of the present invention in a perspective view from top/left side. The stand-alone therapeutic training device (601) is shown in a top/left side view. The housing (602) encapsulates the controller, battery compartment and user feedback units (6, FIG. 1). A transparent cover (607) protects the user feedback units (6, FIG. 1). The user interface (608) is situated on the left side of the housing (602) and may be used for selecting different operational modes of the device and different working ranges for the force/weight scale. A force sensor pad (604) is place on the top surface (112, FIG. 2) of the device (601).

Figure 8:
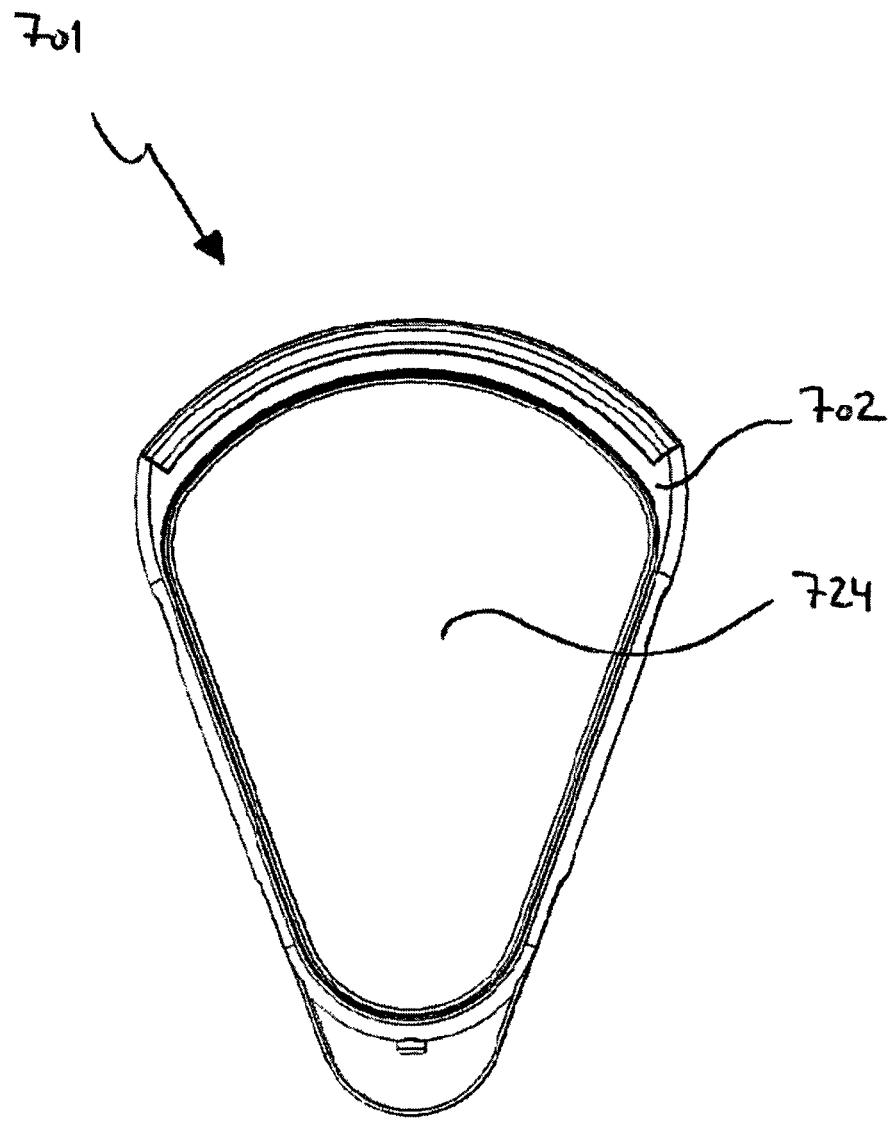
FIG. 8: A second embodiment of the present invention in a perspective view from the bottom side.

Referring to FIG. 8, A second embodiment of the present invention in a perspective view from the bottom. The stand-alone therapeutic training device (701) is shown in a bottom view where the housing (702) and second force sensor can be seen (724).

Figure 9:
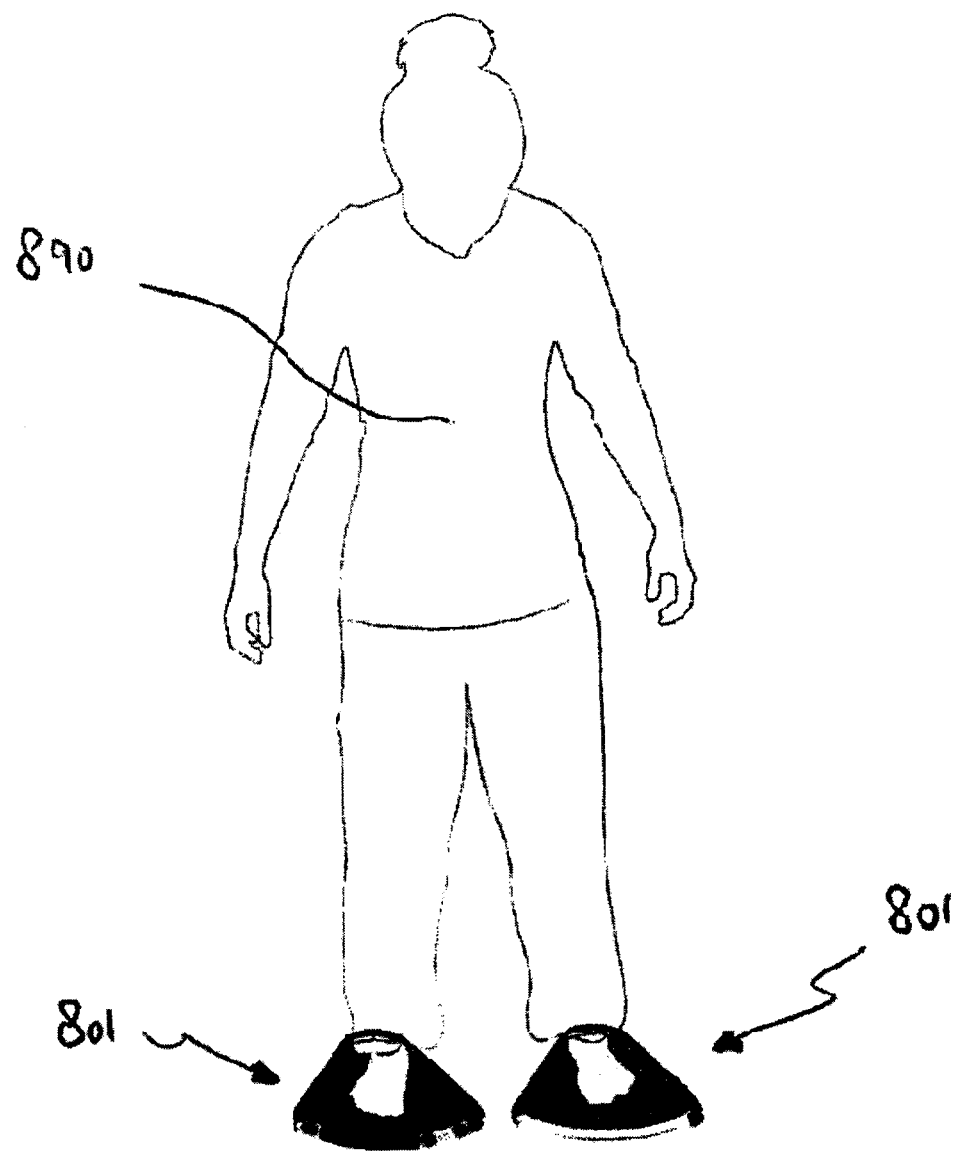
FIG. 9: A user scenario where the present invention is used.

Referring to FIG. 9, A user scenario where the present invention is used. The user (890) stands on two stand-alone therapeutical training devices (801), one foot on each evaluating the weight or force distribution on each leg of the user.

Figure 10:
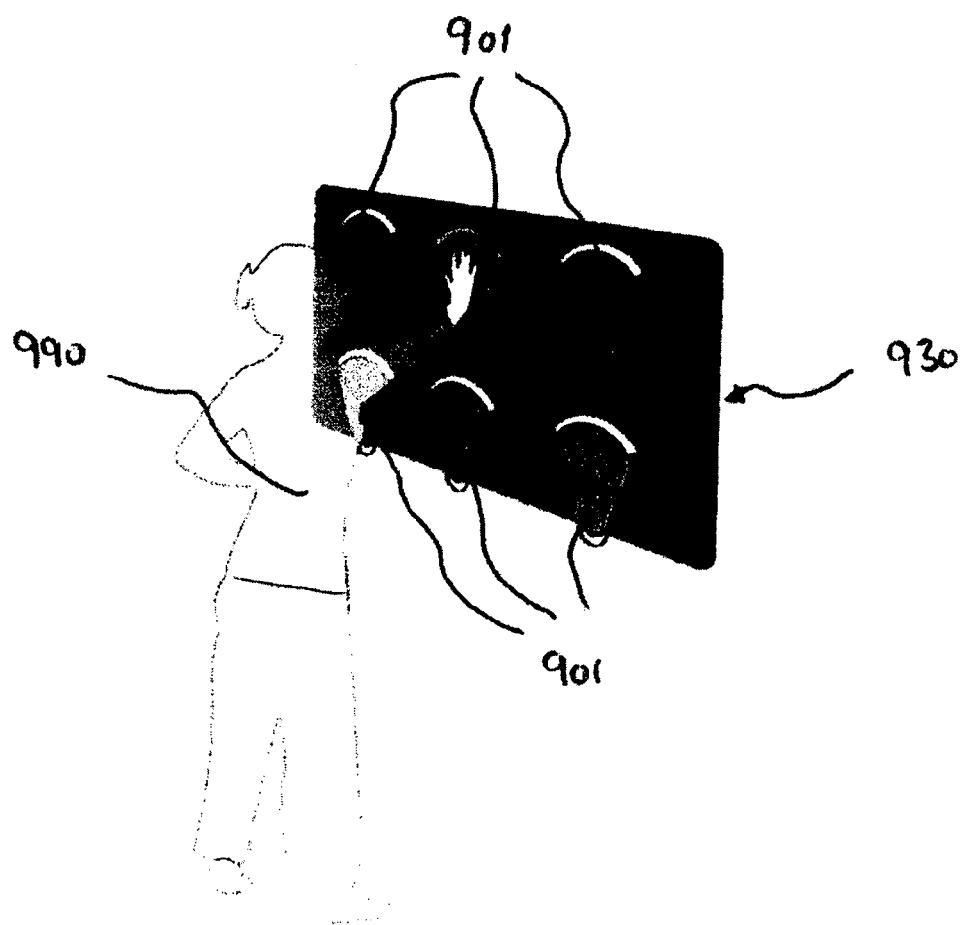
FIG. 10: A second user scenario where the present invention is used.

Referring to FIG. 10, A second user scenario where the present invention is used. A multiple of the stand-alone therapeutical training devices (901) are mounted on a vertical surface (930). The user (990) touches one stand-alone therapeutical training devices (901), giving a random light signal response directing the user (990) to touch the next stand-alone therapeutical training devices (901) with a colour matching the colour of the random light signal indicated.

Figure 11:
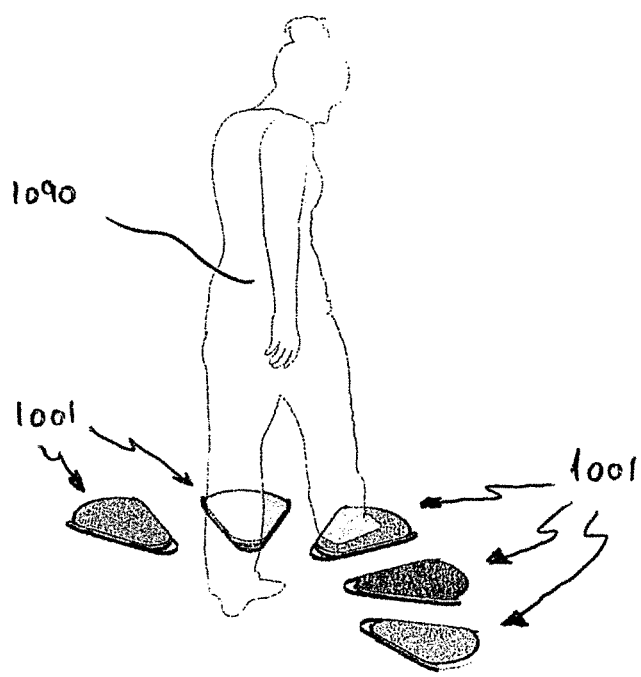
FIG. 11: A third user scenario where the present invention is used.

Referring to FIG. 11, A third user scenario where the present invention is used.

A multiple of the stand-alone therapeutical training devices (1001) are lying on the floor. The user (1090) stands on one stand-alone therapeutical training devices (1001) giving a random light signal response directing the user (1090) to stand on the next stand-alone therapeutical training devices (1001) with a colour matching the colour of the random light signal indicated.

Figure 12:
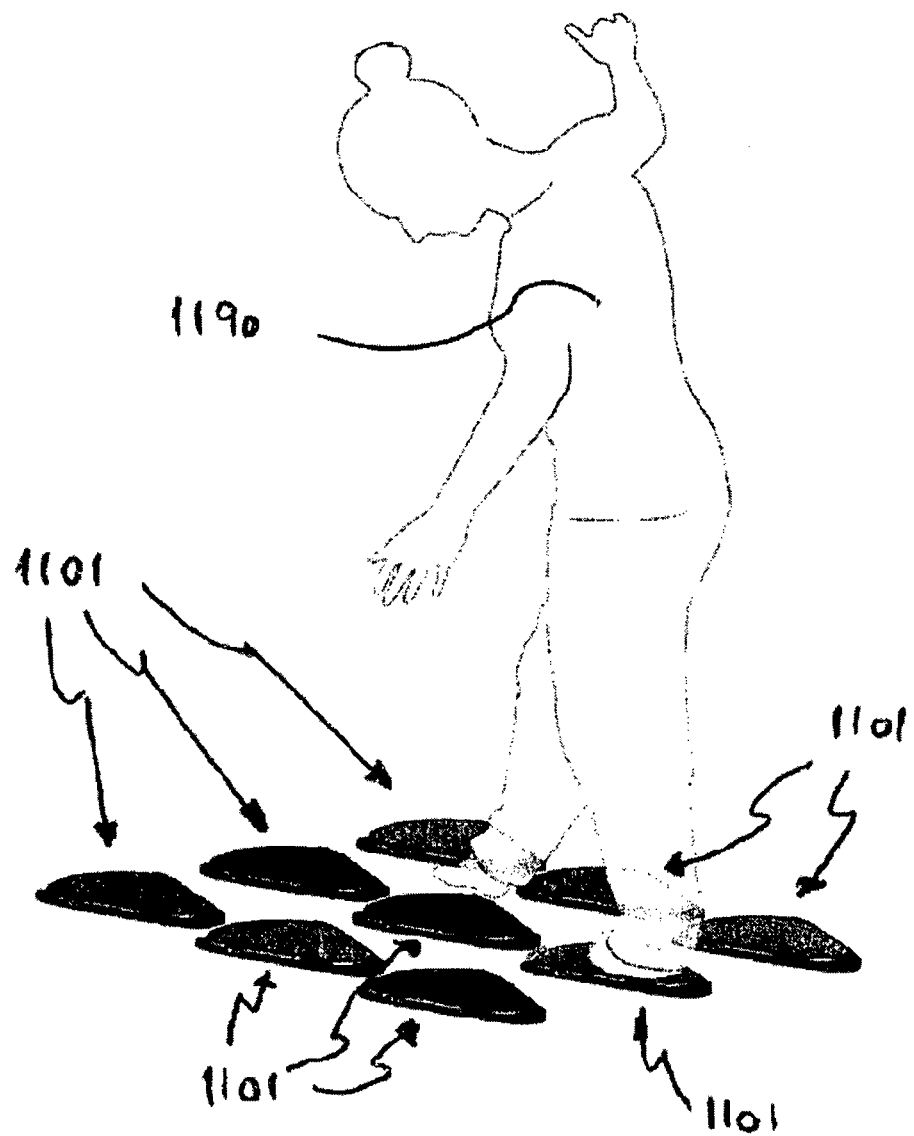
FIG. 12: A fourth user scenario where the present invention is used.

Referring to FIG. 12, A fourth user scenario where the present invention is used.

A multiple of the stand-alone therapeutical training devices (1101) are lying on the floor defining a path of stepping stones. The user (1190) stands on one stand-alone therapeutical training devices (1101) giving a random light signal response directing the user (1190) to stand on the next stand-alone therapeutical training devices (1101) with a colour matching the colour of the random light signal indicated.

Figure 13:
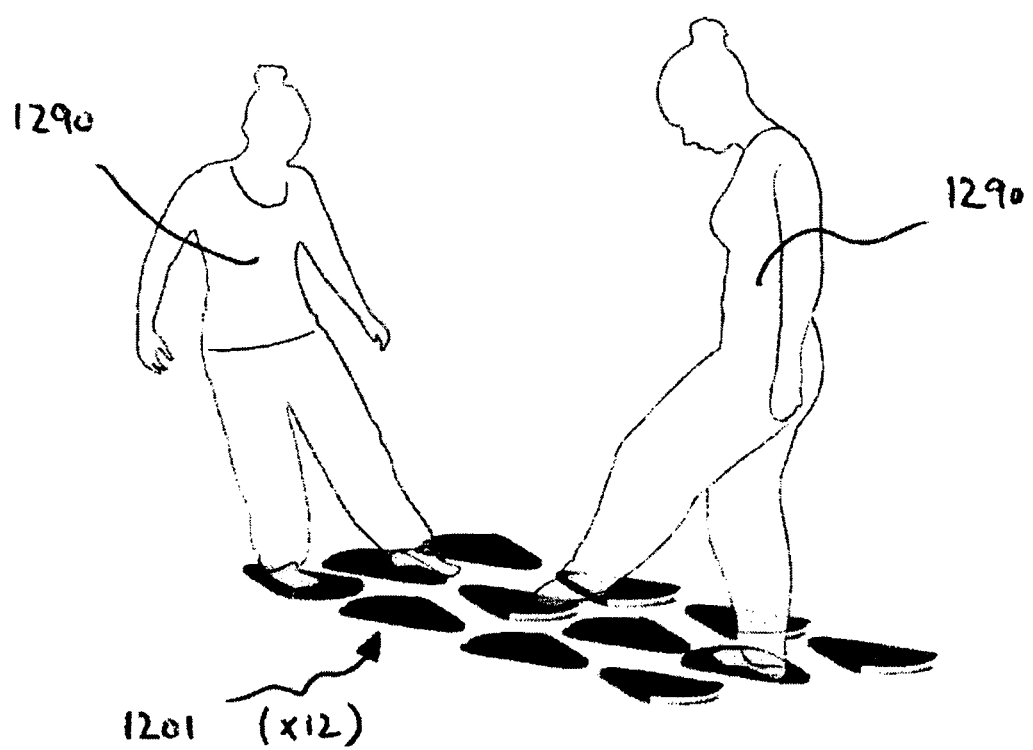
FIG. 13: A fifth scenario where the present invention is used.

Referring to FIG. 13, A fifth user scenario where the present invention is used.

A multiple of the stand-alone therapeutical training devices (1201) are lying on the floor defining a path of stepping stones. Two users (1290) stand on one or more stand-alone therapeutical training devices (1201) giving a random light signal response directing the user (1290) to stand on the next stand-alone therapeutical training devices (1201) with a colour matching the colour of the random light signal indicated.

Figure 14:
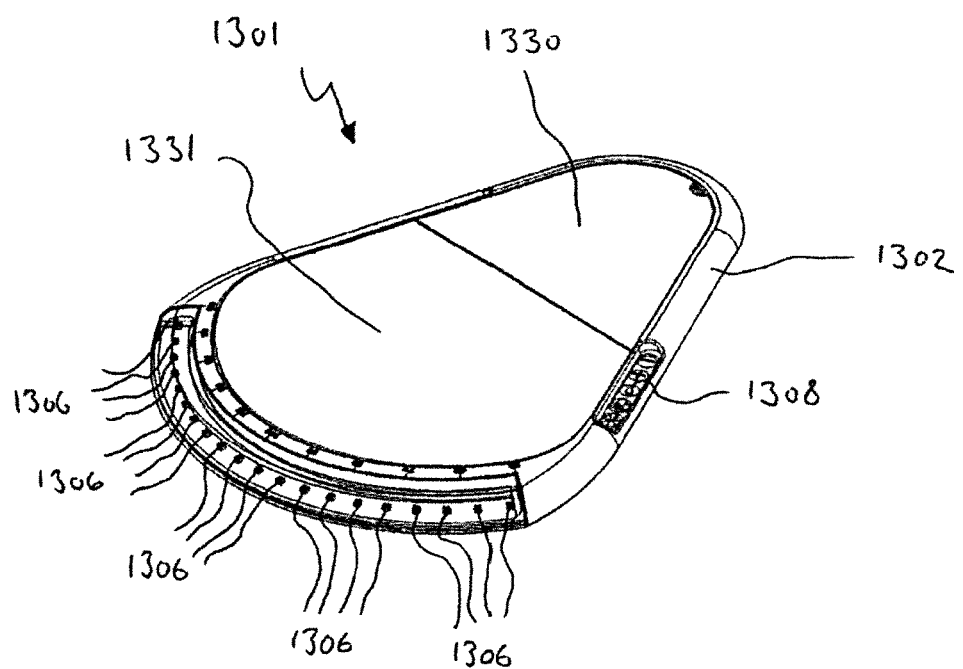
FIG. 14: A third embodiment of the stand-alone therapeutic training device with a force sensor pad with two force sensing areas.

Referring to FIG. 14: A third embodiment of the stand-alone therapeutic training device with a force sensor pad with two force sensing areas. The stand-alone therapeutic training device (1301) is shown in a top/left side view. The housing (1302) encapsulates the controller and user feedback units (1306). A transparent cover (1307) protects the user feedback units (1306). The user interface (1308) is situated on the left side of the housing (1302) and may be used for selecting different operational modes of the device and different working ranges for the force/weight scale. A force sensor pad having two force sensing areas (1330, 1331) configured for sensing the weight and/or force is place on the top surface (112, FIG. 2) of the device (1301). One area (1330) of the force sensor pad is sensing the force applied to one half of the device and another area (1331) of the force sensor pad is sensing the force applied at the other half of the device (1301). The signals obtained at the two sensors are transmitted to the user feedback unit (1306) proportionally to the weight distribution at the heel and toes and/or palm and fingertips of the user.

Figure 15:
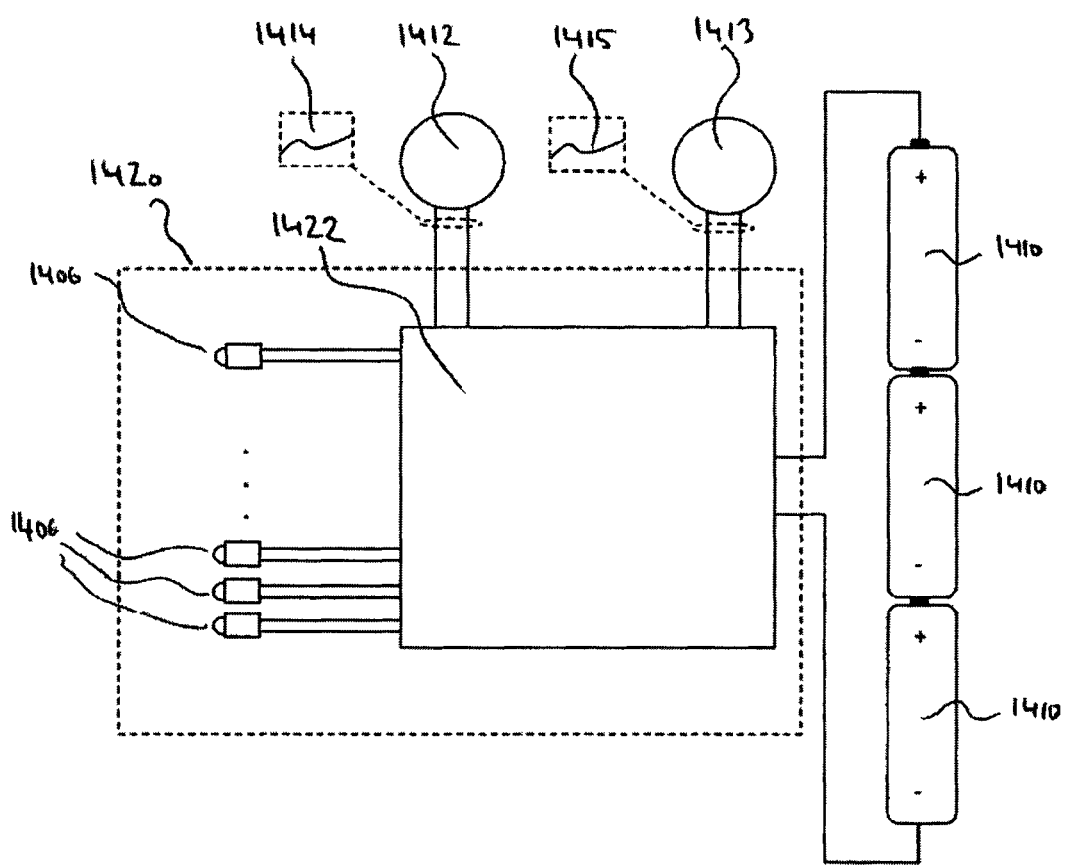
FIG. 15, A block schematic of the electrical system of the present invention where two or more force sensors are implemented.

Referring to FIG. 15, A block schematic of the electrical system of the present invention where two or more force sensors (1412, 1413) are implemented is showing the controller (1420), the batteries (1410) powering the device, the force sensors (1412, 1413), the integrated circuit (1422) and a number of user feedback units (1406). The force sensor (1412, 1413) each generates an electric response signal (1414, 1415) based on the measures force or weight applied to the top surface (112, FIG. 2) of the device (1, FIG. 1), the controller (1420) converts these signals and controls the user feedback units (1406) accordingly. The integrated circuit (1422) is a part of the controller (1420).

The invention claimed is:

1. A therapeutical training system comprising:
a plurality of independently operated training devices, each training device having a shallow housing, the housing having at least a top surface, a bottom surface, and a colored overlay such that the plurality of training devices appear as differently colored platforms selected from a group of predefined colors, said housing of each training device further having at least one force sensor, said force sensor being operative to measure a force applied to said top surface of said housing and to generate a response signal;
at least one user feedback unit; and
a controller disposed inside said housing of each training device, the controller being operative to control the user feedback unit proportionally to said response signal from said force sensor and such that a feedback signal is generated upon activation of the force sensor, wherein the feedback signal corresponds to a color randomly selected from the group of predefined colors thereby directing a user to activate a training device having a colored overlay matching the color of the feedback signal generated.

2. A therapeutical training system according to claim 1, wherein the user feedback unit of each training device comprises at least one light source.

3. A therapeutical training system according to claim 2, wherein the light source includes at least one light emitting diode.

4. A therapeutical training system according to claim 2, wherein the light source comprises a plurality of light emitting diodes, at least two of which emit different colours.

5. A therapeutical training system according to claim 2, wherein the light source comprises at least one multicoloured light emitting diode.

6. A therapeutical training system according to claim 1, wherein the user feedback unit of each training device comprises at least a loudspeaker.

7. A therapeutical training system according to claim 1, wherein the user feedback unit of each training device comprises at least a vibrator.

8. A therapeutical training system according to claim 1, wherein the force sensor of each training device is a force sensitive pad disposed on top of said top surface of said housing.

9. A therapeutical training system according to claim 1, wherein the force sensor of each training device is a strain gauge disposed inside said housing.

10. A therapeutical training system according to claim 1, wherein each training device having at least two force sensors or a force sensor pad with at least two force sensing areas.

11. A therapeutical training system according to claim 10, wherein the controller of each training device further is adapted to control the user feedback unit proportionally to the difference in weight or force applied at at least two force sensors or two force sensing areas.

12. A therapeutical training system according to claim 1, wherein each training device further including a wireless communication operative to transmit the signal obtained at one or more of the force sensors to another device and/or central interface unit.

13. A therapeutical training system according to claim 1, wherein each training device further including a wireless communication operative to receive a signal from another device or central interface unit to control the user feedback unit of the device.

14. Method of providing feedback to a user and/or physiotherapist during training wherein at least the following steps are performed:

a: providing a plurality of therapeutical training devices, each training device comprising a shallow housing, the housing having at least a top surface, a bottom surface and a colored overlay such that the plurality of training devices appear as differently colored platforms selected from a group of predefined colors, b: operating each of the training devices independently, c: performing a measurement of a force applied by the user on the top surface of one of said training devices, d: controlling at least one user feedback unit of said training device based on said measured force applied, e: said feedback unit indicating a force signal to the user which is proportional to the force applied to the top surface of the stand-alone therapeutical training device, and f: indicating a feedback signal to the user when the force is applied by the user on the top surface of said training device, wherein said feedback signal corresponds to a color randomly selected from the group of predefined colors, thereby directing a user to activate a training device having the overlay matching the color of the feedback signal generated.

15. Use of a therapeutical training system according to claim 1 for training or exercising individuals having a need of physical training.

* * * * *